(12) United States Patent
Chalker et al.

(10) Patent No.: US 6,346,395 B1
(45) Date of Patent: *Feb. 12, 2002

(54) **NUCLEIC ACIDS ENCODING *STREPTOCOCCUS PNEUMONIAE* FABG**

(75) Inventors: Alison Francis Chalker, Trappe; Christine Debouck, Wayne; David John Holmes, West Chester; Karen Anne Ingraham, Auburn; Deborah Dee Jaworski, West Chester; Anna Lisa Kosmatka, Doylestown; Damien McDevitt, Berwyn; Jeffrey Mooney, Limerick; Stewart C Pearson, Berwyn; Chi Yong So, Havertwon; Nicola Gail Wallis, Wayne; Min Wang; Richard Lloyd Warren, both of Blue Bell; Yi Yi Zhong, Audubon, all of PA (US)

(73) Assignee: SmithKline Beecham Corp., Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/239,052

(22) Filed: Jan. 27, 1999

(51) Int. Cl.[7] ............................................. C12D 21/06
(52) U.S. Cl. ................... 435/69.1; 435/252.3; 435/320; 435/325; 536/23.1; 536/23.7
(58) Field of Search ............................. 536/23.1, 23.7; 435/69.1, 252.3, 320.1, 325

(56) References Cited

FOREIGN PATENT DOCUMENTS

WO          WO 98/26072          *  6/1998      ................ 536/23.1

OTHER PUBLICATIONS

Morbidoni, et al., "*Bacillus subtilis* Acyl Carrier Protein is Encoded in a Cluster of Lipid Biosynthesis genes.", *SwissProt Submission*, Accession No. P51831, created Oct. 1, 1996.

Zhang, et al., "Transcriptional Analysis of Essential Genes of the *Escherichia coli* Fatty Acid Biosynthesis Gene Cluster by Functional Replacement with the Analogous *Salmonella typhimurium* Gene Cluster.", *Journal of Bacteriology*, vol. 180, No. 13, p. 3295–3303, Jul. 1998.

Morbidoni, et al., "*Bacillus subtilis* Acyl Carrier Protein is Encoded in a Cluster of Lipid Biosynthesis Genes,", *Journal of Bacteriology*, vol. 178, No. 16, p. 4794–4800, Aug., 1996.

Podkovyrov, et al., "Identification of Promoter and Stringent Regulation of Transcription of the fabH, fabD and fabG Genes Encoding Fatty Acid Biosynthetic Enzymes of *Escherichia coli.*", *Nucleic Acids Research*, vol. 24, No. 9, p. 1747–1752, (1996).

* cited by examiner

*Primary Examiner*—Deborah Crouch
*Assistant Examiner*—Richard Schnizer
(74) *Attorney, Agent, or Firm*—Edward R. Gimmi; Thomas S. Deibert; William T. King

(57) ABSTRACT

The invention provides FabG polypeptides and polynucleotides encoding FabG polypeptides and methods for producing such polypeptides by recombinant techniques. Also provided are methods for utilizing FabG polypeptides to screen for antibacterial compounds.

14 Claims, No Drawings

NUCLEIC ACIDS ENCODING *STREPTOCOCCUS PNEUMONIAE* FABG

FIELD OF THE INVENTION

This invention relates to newly identified polynucleotides and polypeptides, and their production and uses, as well as their variants, agonists and antagonists, and their uses. In particular, the invention relates to polynucleotides and polypeptides of the FabG (3-oxoacyl-acyl carrier protein reductase) family, as well as their variants, herein referred to as "FabG," "FabG polynucleotide(s)," and "FabG polypeptide(s)" as the case maybe.

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in act, the genetic material was predicated on the work of Griffith and of Avery, Macleod and McCarty using this microbe. Despite the vast amount of research with *S. pneumoniae*, many questions concerning the virulence of this microbe remain It is particularly preferred to employ Streptococcal genes and gene products as targets for the development of antibiotics.

The frequency of *Streptococcus pneumoniae* infections has risen dramatically in the past few decades. This has been attributed to the emergence of multiply antibiotic resistant strains and an increasing population of people with weakened immune systems. It is no longer uncommon to isolate *Streptococcus pneumoniae* strains that are resists to some or all of the standard antibiotics. This phenomenon has created an unmet medical need and demand for new anti-microbial agents, vaccines, drug screening methods, and diagnostic tests for this organism.

Moreover, the drug discovery process is currently undergoing a fundamental revolution as it embraces "functional genomics," that is, high throughput genome- or gene-based biology. This approach is rapidly superseding earlier approaches based on "positional cloning" and other methods. Functional genomics relies heavily on the various tools of bioinformatics to identify gene sequences of potential interest from the many molecular biology databases now available as well as from other sources. There is a continuing and significant need to identify and characterize further genes and other polynucleotides sequences and their related polypeptides, as targets for drug discovery.

Clearly, there exists a need for polynucleotides and polypeptides, such as the FabG embodiments of the invention, that have a present benefit of among other things, being useful to screen compounds for antimicrobial activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

SUMMARY OF THE INVENTION

The present invention relates to FabG, in particular FabG polypeptides and FabG polynucleotides, recombinant materials and methods for their production. In another aspect, the invention relates to methods for using such polypeptides and polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonist compounds. In a still further aspect, the invention relates to diagnostic assays for detecting diseases associated with microbial infections and conditions associated with such infections, such as assays for detecting FabG expression or activity.

Various changes and modifications within the spirit and scope of the disclosed invention will become readily apparent to those skilled m the art from reading the following descriptions and from reading the other parts of the present disclosure.

DESCRIPTION OF THE INVENTION

The invention relates to FabG polypeptides and polynucleotides as described in greater detail below. In particular, the invention relates to polypeptides and polynucleotides of a FabG of *Streptococcus pneumoniae*, that is related by amino acid sequence homology to *B. subtilis* fabG polypeptide. The invention relates especially to FabG having a nucleotide and amino acid sequences set out in Table 1 as SEQ ID NO:1 and SEQ ID NO:2 respectively. Note that sequences recited in the Sequence Listing below as "DNA" represent an exemplification of the invention, since those of ordinary skill will recognize that such sequences can be usefully employed in polynucleotides in general, including ribopolynucleotides.

TABLE 1

FabG Polynucleotide and Polypeptide Sequences (A) *Streptococcus pneumoniae* FabG polynucleotide sequence [SEQ ID NO:1].
5'-

ATGAAACTAGAACATAAAAATATCTT-
TATTACAGGTTCGAGTCGTGGAATTGGTCTTGCCATCGCCCACAAG

TTTGCTCA

AGCAGGAGCCAACATTGTCTTAAA-
CAGTCGTGGGGCAATCTCAGAAGAATTGCTCGCTGAGTTTTCAAACTA

TGGTATCA

TABLE 1-continued

FabG Polynucleotide and Polypeptide Sequences

AGGTGGTTCCCATTTCAGGAGATGTAT-
CAGATTTTGCAGACGCTAAGCGTATGATTGATCAAGCTATTGCAC

AACTGGGT

TCAGTAGATGTTTTGGTCAACAATG-
CAGGGATTACCCAAGATACTCTTATGCTCAAGATGACAGAAGCAGAT

TTTGAAAA

AGTGCTCAAGGTCAATCTGACTGGTGC-
CTTTAATATGACACAATCAGTCTTGAAACCGATGATGAAAGCCAG

AGAAGGTG

CTATCATTAATATGTCTAGTGTTGTTG-
GTTTGATGGGGAATATTGGTCAAGCTAACTATGCTGCTTCTAAGE

CTGGCTTG

ATTGGCTTTACCAAGTCTGTGGCACGC-
GAGGTCGCTAGTCGGAATATACGAGTCAATGTGATTGCTCCAGGA

ATGATTGA

GTCTGATATGACAGCTATCTTATCA-
GATAAGATTAAGGAAGCTACACTAGCTCAGATTCCGATGAAAGAATT

TGGGCAGG

CAGAGCAGGTTGCAGATTTGACAG-
TATTTTTAGCAGGCCAAGATTATCTAACTGGTCAAGTGATTGCCATTG

ATGGTGGC

TTAAGTATGTAG-3'

(B) *Streptococcus pneumoniae* FabG polypeptide sequence
deduced from a
polynucleotide sequence in this table [SEQ ID NO:2].

NH$_2$-

MKLEHKNIFITGSSRGIGLAIAHKFAQA-
GANIVLNSRGAISEELLAEFSNYGIKVVFISGDVSDFADAKRMI

DQAIAELG

SVDVLVNNAGITQDTLMLKMTEADFEKV-
LKVNLTGAFNMTQSVLKPMMKAREGAIINMSSVVGLMGNIGQAN

YAASKAGL

IGFTKSVAREVASRNIRVNVIAFGMIES-
DMTAILSDKIKEATLAQIPMKEFGQAEQVADLTVFLAGQDYLTG

QVIAIDGG

LSM*-COOH

Deposited materials

A deposit comprising a *Streptococcus pneumoniae* 0100993 stain has been deposited with the National Collections of Industrial and Marine Bacteria Ltd. (herein "NCIMB"), 23 St. Machar Drive, Aberdeen AB2 1RY, Scotland on 11 April 1996 and assigned deposit number 40794. The deposit was described as *Streptococcus pneumoniae* 0100993 on deposit. On 17 April 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain comprises a fills length FabG gene. The sequence of the polynucleotides comprised in the deposited stain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent The deposited stain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecule encoding a mature polypeptide expressible by the *Streptococcus pneumoniae* 0100993 strain, which polypeptide is comprised in he deposited strain. Further provided by the invention are FabG polynucleotide sequences in the deposited strain, such as DNA and RNA, and amino acid sequences encoded thereby. Also provided by the invention are FabG polypeptide and polynucleotide sequences isolated from the deposited strain.

Polypeptides

FabG polypeptide of the invention is substantially phylogenetically related to other proteins of the fabG (3-oxoacyl-acyl carrier protein reductase) family.

In one aspect of the invention there are provided polypeptides of *Streptococcus pneumoniae* referred to herein as "FabG" and "FabG polypeptides" as well as biologically, diagnostically, prophylactically, clinically or therapeutically useful variants thereof, and compositions comprising the same.

Among the particularly preferred embodiments of the invention are variants of FabG polypeptide encoded by naturally occurring alleles of a FabG gene.

The present invention further provides for an isolated polypeptide that: (a) comprises or consists of an amino acid sequence that has at least 95% identity, most preferably at least 97–99% or exact identity, to that of SEQ ID NO:2 over the entire length of SEQ ID NO:2; (b) a polypeptide encoded by an isolated polynucleotide comprising or consisting of a polynucleotide sequence that has at least 95% identity, even more preferably at least 97–99% or exact identity to SEQ ID NO:1 over the entire length of SEQ ID NO:1; (c) a polypeptide encoded by an isolated polynucleotide comprising or consisting of a polynucleotide sequence encoding a polypeptide that has at least 95% identity, even more preferably at least 97–99% or exact identity, to the amino acid sequence of SEQ ID NO:2, over the entire length of SEQ ID NO:2.

The polypeptides of the invention include a polypeptide of Table 1 [SEQ ID NO:2] (in particular a mature polypeptide) as well as polypeptides and fragments, particularly those that has a biological activity of FabG, and also those that have at least 95% identity to a polypeptide of Table 1 [SEQ ID NO:2] and also include portions of such polypeptides with such portion of the polypeptide generally comprising at least 30 amino acids and more preferably at least 50 amino acids.

The invention also includes a polypeptide consisting of or comprising a polypeptide of the formula:

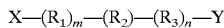

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof In the formula above, $R_2$ is oriented so that its amino terminal amino acid residue is at the led covalently bound to $R_1$, and its carboxy terminal ammo acid residue is at the right, covalently bound to $R_3$. Any stretch of amino acid residues denoted by either $R_1$ or $R_3$, where m and/or n is greater than 1, may be either a heropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from *Streptococcus pneumoniae*, however, it may preferably be obtained from other organisms of the same taxonomic genus. A polypeptide of the invention may also be obtained, for example, from organisms of the same taxonomic family or order.

A fragment is a variant polypeptide having an amino acid sequence that is entirely the same as part but not all of any amino acid sequence of any polypeptide of the invention. As with FabG polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of Table 1 [SEQ ID NO:2], or of variants thereof, such as a continuous series of residues that includes an amino- and/or carboxyl-terminal amino acid sequence. Degradation forms of the polypeptides of the invention produced by or in a host cell particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface- forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2, or an isolated polypeptide comprising an amino acid sequence having at least 15, 20, 30, 40, 50 or 100 contiguous amino acids truncated or deleted from the amino acid sequence of SEQ ID NO:2.

Fragments of the polypeptides of the invention may be employed for producing the corresponding full-length polypeptide by peptide synthesis; therefore, these variants may be employed as intermediates for producing the full-length polypeptides of the invention.

Polynucleotides

It is an object of the invention to provide polynucleotides that encode FabG polypeptides, particularly polynucleotides that encode a polypeptide herein designated FabG.

In a particularly preferred embodiment of the invention the polynucleotide comprises a region encoding FabG polypeptides comprising a sequence set out in Table 1 [SEQ ID NO:1] that includes a full-length gene, or a variant thereof. The Applicants believe that this full length gene is essential to the growth and/or survival of an organism that possesses it, such as *Streptococcus pneumoniae*.

As a further aspect of the invention there are provided isolated nucleic acid molecules encoding and/or expressing FabG polypeptides and polynucleotides, particularly *Streptococcus pneumoniae* FabG polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one fill length gene, that encodes a FabG polypeptide having a deduced amino acid sequence of Table 1 [SEQ ID NO:2] and polynucleotides closely related thereto and variants thereof.

In another particularly preferred embodiment of the invention there is a FabG polypeptide from *Streptococcus pneumoniae* comprising or consisting of an amino acid sequence of Table 1 [SEQ ID NO:2], or a variant thereof.

Using the information provided herein, such as a polynucleotide sequence set out in Table 1 [SEQ ID NO:1], a polynucleotide of the invention encoding FabG polypeptide may be obtained using standard coloring and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as a polynucleotide sequence given in Table 1 [SEQ ID NO:1], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). see in particular Screening By Hybridization 1.90 and Sequencing Denatured Double-Stranded DNA Templates 13.70). Direct genomic DNA sequencing may also be performed to obtain a fill length gene sequence. Illustrative of the invention, each polynucleotide set out in Table 1 [SEQ ID NO:1] was discovered in a DNA library derived from *Streptococcus pneumoniae* 0100993.

Moreover, each DNA sequence set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known to those skilled in the art. The polynucleotide of SEQ ID NO:1, between nucleotide number 1 and the stop codon that begins at nucleotide number 730 of SEQ ID NO:1, encodes the polypeptide of SEQ ID NO:2.

In a further aspect, the present invention provides for an isolated polynucleotide comprising or consisting of: (a) a polynucleotide sequence that has at least 95% identity, even more preferably at least 97–99% or exact identity to SEQ ID NO:1 over the entire length of SEQ ID NO:1, or the entire length of that portion of SEQ ID NO:1 which encodes SEQ ID NO:2; (b) a polynucleotide sequence encoding a polypeptide t has at least 95% identity, even more preferably at least 97–99% or 100% exact, to the amino acid sequence of SEQ ID NO:2, over the entire length of SEQ ID NO:2.

A polynucleotide encoding a polypeptide of the present invention, including homologs and orthologs from species other than *Streptococcus pneumoniae*, may be obtained by a process that comprises the steps of screening an appropriate library under stringent hybridization conditions with a labeled or detectable probe consisting of or comprising the sequence of SEQ ID NO:1 or a fragment thereof, and isolating a full-length gene and/or genomic clones comprising said polynucleotide sequence.

The invention provides a polynucleotide sequence identical over its entire length to a coding sequence (open reading frame) in Table 1 [SEQ ID NO:1]. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or pre protein sequence. The polynucleotide of the invention may also comprise at least one non-coding sequence, including for example, but not limited to at least one non-coding 5' and 3' sequence, such as the transcribed but non-translated sequences, termination signals (such as rhodependent and rho-independent termination signals), ribosome binding sites, Kozak sequences, sequences that stabilize MRNA, introns, and polyadenylation signals. The polynucleotide sequence may also comprise additional coding sequence encoding additional amino acids. For example, a marker sequence that facilitates purification of a fused polypeptide can be encoded. In certain embodiments of the invention, the marker sequence is a hexa-histidine peptide, as provided in the pQE vector (Qiagen, Inc.) and described in Gentz et al., *Proc. Natl, Acad. Sci., USA* 86: 821–824 (1989), or an HA peptide tag (Wilson et al, *Cell* 37: 767 (1984), both of that may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotide 1 to the nucleotide immediately upstream of or including nucleotide 730 set forth in SEQ ID NO:1 of Table 1, both of that encode a FabG polypeptide.

The invention also includes a polynucleotide consisting of or comprising a polynucleotide of the formula:

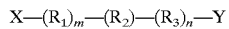

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero , n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, that can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integerbetween 1 and 50, 100, or 500.

It is most preferred that a polynucleotide of the invention is derived from *Streptococcus pneumoniae*, however, it may preferably be obtained from other organisms of the same taxonomic genus. A polynucleotide of the invention may also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* FabG having an amino acid sequence set out in Table 1 [SEQ ID NO:2]. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may comprise coding and/or noncoding sequences.

The invention further relates to variants of the polynucleotides described herein that encode variants of a polypeptide having a deduced amino acid sequence of Table 1 [SEQ ID NO:2]. Fragments of polynucleotides of the invention may be used, for example, to synthesize full-length polynucleotides of the invention.

Further particularly preferred embodiments are polynucleotides encoding FabG variants, that have the amino acid sequence of FabG polypeptide of Table 1 [SEQ ID NO:2] in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of FabG polypeptide.

Preferred isolated polynucleotide embodiments also include polynucleotide fragments, such as a polynucleotide comprising a nucleic acid sequence having at least 15, 20, 30, 40, 50 or 100 contiguous nucleic acids from the polynucleotide sequence of SEQ ID NO:1, or an polynucleotide comprising a nucleic acid sequence having at least 15, 20, 30, 40, 50 or 100 contiguous nucleic acids truncated or deleted from the 5' and/or 3' end of the polynucleotide sequence of SEQ ID NO:1.

Further preferred embodiments of the invention are polynucleotides that are at least 95% or 97% identical over their entire length to a polynucleotide encoding FabG polypeptide having an amino acid sequence set out in Table 1 [SEQ NO:2], and polynucleotides that are complementary to such polynucleotides. Most highly preferred are polynucleotides that comprise a region that is at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as a mature polypeptide encoded by a DNA of Table 1 [SEQ ID NO:9 .

In accordance with certain preferred embodiments of this invention there are provided polynucleotides Hat hybridize, particularly under stringent conditions, to FabG polynucleotide sequences, such as those polynucleotides in Table 1.

The invention further relates to polynucleotides that hybridize to he polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library comprising a complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding FabG and to isolate cDNA and genomic clones of other genes that have a high identity, particularly high sequence identity, to a FabG gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have lee than 30 nucleotide residues or base pairs.

A coding region of a FabG gene may be isolated by screening using a DNA sequence provided in Table 1 [SEQ ID NO:1] to synthesize an oligonucleotide probe. A labeled oligonucleotide having a sequence complementary to that of a gene of the invention is then used to screen a library of cDNA, genomic DNA or MRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et a., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as farther discussed herein relating to polynucleotide assays.

The polynucleotides of the invention that are oligonucleotides derived from a sequence of Table 1 [SEQ ID NOS:1 or 2] may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is a mature protein plus additional amino or carboxyl-terminal amino acids, or amino acids interior to a mature polypeptide (when a mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from a mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

As will be recognized, the entire polypeptide encoded by an open reading frame is often not required for activity. Accordingly, it has become routine in molecular biology to map the boundaries of the primary structure required for activity with N-terminal and C-terminal deletion experiments. These experiments utilize exonuclease digestion or convenient restriction sites to cleave coding nucleic acid sequence. For example, Promega (Madison, Wis.) sell an Erase-a-base™ system that uses Exonuclease III designed to facilitate analysis of the deletion products (protocol available at www.promegacom). The digested endpoints can be repaired (eg., by ligation to synthetic linkers) to the extent necessary to preserve an open reading frame. In this way, the nucleic acid of SEQ ID NO:1 readily provides contiguous fragments of SEQ ID NO:2 sufficient to provide an activity, such as an enzymatic, binding or antibody-inducing activity. Nucleic acid sequences encoding such fragments of SEQ ID NO:2 and variants thereof as described herein are within the invention, as are polypeptides so encoded.

In sum, a polynucleotide of the invention may encode a mature protein plus a leader sequence (which may be referred to as a preprotein), a precursor of a mature protein having one or more prosequences that are not the leader sequences of a preprotein, or a preproprotein, that is a precursor to a proprotein, having a leader sequence and one or more prosequences, that generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells that are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci *E. coli*, streptomyces, cyanobacteria, *Bacillus sublitis*, and *Streptococcus pneumoniae*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids. The expression system constructs may comprise control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et a., *MOLECULAR CLONING, A LABORATORY MANUAL*, (supra).

In recombinant expression systems in eukaryotes, for secretion of a translated protein into the lumen of the endoplasmic reticulum, into the periplasmic space or into Me extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic, Prognostic, Serotyping and Mutation Assays

This invention is also related to the use of FabG polynucleotides and polypeptides of the invention for use as diagnostic reagents. Detection of FabG polynucleotides and/or polypeptides in a eukaryote, particularly a mammal and especially a human, will provide a diagnostic method for diagnosis of disease, staging of disease or response of an infectious organism to drugs. Eukaryotes, particularly mammals, and especially humans, particularly those infected or suspected to be infected with an organism comprising the FabG gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled FabG polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397–4401 (1985).

In another embodiment, an array of oligonucleotides probes comprising FabG nucleotide sequence or fragments thereof can be constructed to conduct efficient screening of, for example, genetic mutations, serotype, taxonomic classification or identification Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit that comprises: (a) a polynucleotide of the present invention, preferably the nucleotide sequence of SEQ ID NO:1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2. It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferable, SEQ ID NO:1, that is associated with a disease or pathogenicity will provide a diagnostic tool that can add to, or define, a diagnosis of a disease, a prognosis of a course of disease, a determination of a stage of disease, or a susceptibility to a disease, that results from under expression, over-expression or altered expression of the polynucleotide. Organisms, particularly infectious organisms, carrying mutations in such polynucleotide may be detected at the polynucleotide level by a variety of techniques, such as those described elsewhere herein.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding FabG polypeptide can be used to identify and analyze mutations. The invention further provides these primers with 1, 2, 3 or 4 nucleotides removed from the 5' and/or the 3' end. These primers may be used for, among other things, amplifying FabG DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by *Streptococcus pneumoniae*, comprising determining from a sample derived from an individual, such as a bodily material, an increased level of expression of polynucleotide having a sequence of Table 1 [SEQ ID NO:1]. Increased or decreased expression of a FabG polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of FabG polypeptide compared to normal control tissue samples may be used to detect the presence of an infection, for example. Assay techniques that can be used to determine levels of a FabG polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

Polypeptides and polynucleotides of the present invention are responsible for many biological functions, including many disease states, in particular the Diseases herein mentioned. It is therefore desirable to devise screening methods to identify compounds that agonize (e.g, stimulate) or that antagonize (e.g., inhibit) the function of the polypeptide or polynucleotide. Accordingly, in a further aspect, the present invention provides for a method of screening compounds to identify those that agonize or that antagonize the function of a polypeptide or polynucleotide of the invention, as well as related polypeptides and polynucleotides. In general, agonists or antagonists (e.g., inhibitors) may be employed for therapeutic and prophylactic purposes for such Diseases as herein mentioned. Compounds may be identified from a variety of sources, for example, cells, cell-free preparations, chemical libraries, and natural product mixtures. Such agonists and antagonists so-identified may be natural or modified substrates, ligands, receptors, enzymes, etc., as the case may be, of FabG polypeptides and polynucleotides; or may be structural or functional mimetics thereof (see Coligan et al., *Current Protocols in Immunology* 1(2):Chapter 5 (1991)).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists, in the absence of an agonist or antagonist, by testing whether the candidate compound results in inhibition of activation of the polypeptide or polynucleotide, as the case may be. Further, the screening methods may simply comprise the steps of mixing a candidate compound with a solution comprising a polypeptide or polynucleotide of the present invention, to form a mixture, measuring FabG polypeptide and/or polynucleotide activity in the mixture, and comparing the FabG polypeptide and/or polynucleotide activity of the mixture to a standard. Fusion proteins, such as those made from Fc portion and FabG polypeptide, as herein described, can also be used for high-throughput screening assays to identify antagonists of the polypeptide of the present invention, as well as of phylogenetically and/or functionally related polypeptides (see D. Bennett et al., J Mol Recognition, 8:52–58 (1995); and K. Johanson et al., J Biol Chem, 270(16):9459–9471 (1995)).

The polynucleotides, polypeptides and antibodies that bind to and/or interact with a polypeptide of the present invention may also be used to configure screening methods for detecting the effect of added compounds on the production of MRNA and/or polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

The invention also provides a method of screening compounds to identify those that enhance (agonist) or block (antagonist) the action of FabG polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising FabG polypeptide and a labeled substrate or ligand of such polypeptide is incubated in the absence or the presence of a candidate molecule that may be a FabG agonist or antagonist. The ability of the candidate molecule to agonize or antagonize the FabG polypeptide is reflected in decreased binding of the labeled ligand or decreased production of product from such substrate. Molecules that bind gratuitously, i.e., without inducing the effects of FabG polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product a reporter gene that is responsive to changes in FabG polynucleotide or polypeptide activity, and binding assays known in the art.

Polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, $^{125}I$), chemically modified (for instance, biotinylated), or fused to a peptide sequence suitable for detection or purification, and incubated with a source of the putative receptor (e.g., cells, cell membranes, cell supernatants, tissue extracts, bodily materials). Other methods include biophysical techniques such as surface plasmon resonance and spectroscopy. These screening methods may also be used to identify agonists and antagonists of the polypeptide that compete with the binding of the polypeptide to its receptor(s), if any. Standard methods for conducting such assays are well understood in the art.

The fluorescence polarization value for a fluorescently-tagged molecule depends on the rotational correlation time or tumbling rate. Protein complexes, such as formed by FabG polypeptide associating with another FabG polypeptide or other polypeptide, labeled to comprise a fluorescently-labeled molecule will have higher polarization values than a fluorescently labeled monomeric protein. It is preferred that this method be used to characterize small molecules that disrupt polypeptide complexes.

Fluorescence energy transfer may also be used characterize small molecules that interfere with the formation of FabG polypeptide dimers, trimers, tetramers or higher order structures, or structures formed by FabG polypeptide bound to another polypeptide. FabG polypeptide can be labeled with both a donor and acceptor fluorophore. Upon mixing of the two labeled species and excitation of the donor fluorophore, fluorescence energy transfer can be detected by observing fluorescence of the acceptor. Compounds that block dimerization will inhibit fluorescence energy transfer.

Surface plasmon resonance can be used to monitor the effect of small molecules on FabG polypeptide self-association as well as an association of FabG polypeptide and another polypeptide or small molecule. FabG polypeptide can be coupled to a sensor chip at low site density such that covalently bound molecules will be monomeric. Solution protein can then passed over the FabG polypeptide-coated surface and specific binding can be detected in real-time by monitoring the change in resonance angle caused by a change in local refractive index. This technique can be used to characterize the effect of small molecules on kinetic rates and equilibrium binding constants for FabG polypeptide self-association as well as an association of FabG polypeptide and another polypeptide or small molecule.

A scintillation proximity assay may be used to characterize the interaction between an association of FabG polypeptide with another FabG polypeptide or a different polypeptide. FabG polypeptide can be coupled to a scintillation-filled bead. Addition of radio-labeled FabG polypeptide results in binding where the radioactive source molecule is in close proximity to the scintillation fluid. Thus, signal is emitted upon FabG polypeptide binding and compounds that prevent FabG polypeptide self-association or an association of FabG polypeptide and another polypeptide or small molecule will diminish signal.

In other embodiments of the invention there are provided methods for identifying compounds that bind to or otherwise interact with and inhibit or activate an activi or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Another example of an assay for FabG agonists is a competitive assay that combines FabG and a potential agonist with FabG-binding molecules, recombinant FabG binding molecules, natural substrates or ligands, or substrate or ligand mimetics, under appropriate conditions for a competitive inhibition assay. FabG can be labeled, such as by radioactivity or a colorimetric compound, such that the number of FabG molecules bound to a binding molecule or converted to product can be determined accurately to assess the effectiveness of the potential antagonist.

It will be readily appreciated by the skilled artisan that a polypeptide and/or polynucleotide of the present invention may also be used in a method for the structure-based design of an agonist or antagonist of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist or antagonist; (c) synthesizing candidate compounds that are predicted to bind to or react with the deduced binding site(s), reactive site(s), and/or motif(s); and (d) testing whether the candidate compounds are indeed agonists or antagonists. It will be further appreciated that this will normally be an iterative process, and this iterative process may be performed using automated and computer-controlled steps.

In a father aspect, the present invention provides methods of treating abnormal conditions such as, for instance, a Disease, related to either an excess of, an under expression of, an elevated activity of, or a decreased activity of FabG polypeptide and/or polynucleotide.

If the expression and/or activity of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragments of the FabG polypeptide and/or polypeptide.

In still another approach, expression of the gene encoding endogenous FabG polypeptide can be inhibited using expression blocking techniques. This blocking may be targeted against any step in gene expression, but is preferably targeted against transcription and/or translation. An examples of a known technique of this sort involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides that form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mnRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial FabG proteins that mediate tissue damage and/or; to block the normal progression of pathogenesis in infections initiated other than by the implantation of in-dwelling devices or by other surgical techniques.

In accordance with yet another aspect of the invention, there are provided FabG agonists and antagonists, preferably bacteristatic or bactericidal agonists and antagonists.

The antagonists and agonists of the invention may be employed, for instance, to prevent, inhibit and/or treat diseases.

*Helicobacter pylori* (herein "*H. pylori*") bacteria infect the stomachs of over one-third of the world's population causing stomach cancer, ulcers, and gastritis (International Agency for Research on Cancer (1994) *Schistosomes, Liver Flukes and Helicobacter Pylori* (International Agency for Research on Cancer, Lyon, France, http://www.uicc.ch/ecp/ecp2904.htm). Moreover, the International Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of FabG polypeptides and/or polynucleotides) found using screens provided by the invention, or known in the art, particularly narrow-spectrum antibiotics, should be useful in the treatment of *H. pylori* infection. Such treatment should decrease the advent of *H. pylori*-induced cancers, such as gastrointestinal carcinoma. Such treatment should also prevent, inhibit and/or cure gastric ulcers and gastritis.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

GLOSSARY

The following definitions are provided to facilitate understanding of certain terms used frequently herein.

"Bodily material(s) means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

"Disease(s)" means any disease caused by or related to infection by a bacteria, including, for example, otitis media, conjunctivitis, pneumonia, bacteremia, meningitis, sinusitis, pleural empyema and endocarditis, and most particularly meningitis, such as for example infection of cerebrospinal fluid. "Host cell(s)" is a cell that has been introduced (e.g., transformed or transfected) or is capable of introduction (e.g., transformation or transfection) by an exogenous polynucleotide sequence. "Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following: Algorithm: Needleman and Wunsch, J. Mol Biol. 48: 443–453 (1970) Comparison matrix: BLOSUM62 from Hentikoff and Hentikoff, *Proc. Natl. Acad. Sci. USA*. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a-(x_a \cdot y),$$

wherein $n_a$ is the number of amino acid alterations, $x_a$ is the total number of amino acids in SEQ ID NO:2, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

"Individual(s)" means a multicellular eudaryote, including, but not limited to a metazoan, a mandal,an ovid, a bovid, a simian, a primate, and a human.

"Isolated" means altered "by the hand of man" from its natural state, i.e., if it occurs in nature, it has been changed or removed from its original environment4 or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterti, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum Rickettsia rickettsii* and *Chlamydia trachomitis*, (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis*, or *Candida albicans*.

"Polynucleotide(s)" generally refers to any polyribonucleotide or polydeoxynbonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mix of single- and double-stranded regions, hybrid molecules comprising DNA and RNA that may be single-stranded or, more typically, double-stranded, or triplestranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules.

The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of sill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by aural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, aceyation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteme, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifur et al., *Meth Enzymol*. 182:626–646 (1990) and Rattan et al., *Protein Synthesis: Posttranslational Modifications and Aging*, Ann N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from e referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gin; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, that are well known and routine to those of skill in the art, except where otherwise described in detail. The examples are illustrative, but do not limit the invention.

Example 1

Strain selection, Library Production and Sequencing

The polynucleotide having a DNA sequence given in Table 1 [SEQ ID NO:1] was obtained from a library of clones of chromosomal DNA of *Streptococcus pneumoniae* in *E. coli*. The sequencing data from two or more clones comprising overlapping *Streptococcus pneumoniae* DNAs was used to construct the contiguous DNA sequence in SEQ ID NO:1. Libraries may be prepared by routine methods, for example: Methods 1 and 2 below.

Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

FabG Characterization

FabG Essentiality testing:

An allelic replacement cassette consists of a pair of 500 bp chromosomal DNA fragments flanking an erythromycin resistance gene. The chromosomal DNA sequences are usually the 500 bp preceding and following the gene of interest.

Attempts are made to introduce the allelic replacement cassette into *S. pneumoniae* R6 or *S. pneumoniae* 100993 by transformation. Competent cells are prepared according to published protocols. DNA is introduced into the cells by incubation of 500 ng of allelic replacement cassette with $10^6$ cells at 30° C. for 30 minutes. The cells are transferred to 37° C. for 90 minutes to allow expression of the erythromycin resistance gene. Cells are plated in agar containing 1ug erythromycin per ml. Following incubation at 37° C. for 36 hours, any observed colonies are picked and grown overnight in Todd-Hewitt broth supplemented with 0.5% yeast extract. Typically, in positive control experiments carried out in parallel which target a non-essential gene, $10^2$–$10^3$ transformants containing the appropriate allelic replacement are obtained. If erythromycin resistant colonies are only observed in transformation experiments using *S. pneumoniae* R6, DNA from these cells are used to transform *S. pneumoniae* 100993. The transformation procedure is identical to that for *S. pneumoniae* R6 except that a competence stimulating heptadecapeptide (Havarstein et al., (1995) P.N.A.S. 92, 11140–11144) is added at a concentration of 1 ug/ml in the initial transformation mix. Mutants are selected by their ability to grow in agar containing 1 ug erythromycin per ml. No transformants were obtained in three separate transformation experiments using an allelic replacement cassette that would eliminate fabG. Consequently, the gene is considered as being essential in vitro.

What is claimed is:

1. An isolated polynucleotide segment comprising a nucleic acid sequence, wherein the nucleic acid sequence encodes a polypeptide comprising SEQ ID NO:2.

2. A vector comprising the isolated polynucleotide of claim 1.

3. An isolated host cell comprising the vector of claim 2.

4. A process for producing a polypeptide comprising culturing the host cell of claim 3 under conditions sufficient for production of the polypeptide, which polypeptide comprises SEQ ID NO:2.

5. An isolated polynucleotide segment comprising a nucleic acid sequence, wherein the nucleic acid sequence encodes a polypeptide consisting of SEQ ID NO:2.

6. A vector comprising the isolated polynucleotide of claim 5.

7. An isolated host cell comprising the vector of claim 6.

8. A process for producing a polypeptide comprising culturing the host cell of claim 7 under conditions sufficient for production of the polypeptide, which polypeptide consists of SEQ ID NO:2.

9. An isolated polynucleotide segment comprising the full complement of the entire length of the nucleic acid sequence of claim 1.

10. A vector comprising the isolated polynucleotide of claim 9.

11. An isolated host cell comprising the vector of claim 10.

12. An isolated polynucleotide segment comprising the full complement of the entire length of the nucleic acid sequence of claim 5.

13. A vector comprising the isolated polynucleotide of claim 12.

14. An isolated host cell comprising the vector of claim 13.

* * * * *

SEQUENCE LISTING

```
<160> NUMBER OF SEQ ID NOS: 2

<210> SEQ ID NO 1
<211> LENGTH: 732
<212> TYPE: DNA
<213> ORGANISM: Streptococcus pneumoniae

<400> SEQUENCE: 1
atgaaactag aacataaaaa tatctttatt acaggttcga gtcgtggaat tggtcttgcc      60
atcgcccaca agtttgctca agcaggagcc aacattgtct taaacagtcg tggggcaatc     120
tcagaagaat tgctcgctga gttttcaaac tatggtatca aggtggttcc catttcagga     180
gatgtatcag attttgcaga cgctaagcgt atgattgatc aagctattgc agaactgggt     240
tcagtagatg ttttggtcaa caatgcaggg attacccaag atactcttat gctcaagatg     300
acagaagcag attttgaaaa agtgctcaag gtcaatctga ctggtgcctt taatatgaca     360
caatcagtct tgaaaccgat gatgaaagcc agagaaggtg ctatcattaa tatgtctagt     420
gttgttggtt tgatggggaa tattggtcaa gctaactatg ctgcttctaa ggctggcttg     480
attggcttta ccaagtctgt ggcacgcgag gtcgctagtc ggaatatacg agtcaatgtg     540
attgctccag gaatgattga gtctgatatg acagctatct tatcagataa gattaaggaa     600
gctacactag ctcagattcc gatgaaagaa tttgggcagg cagagcaggt tgcagatttg     660
acagtatttt tagcaggcca agattatcta actggtcaag tgattgccat tgatggtggc     720
ttaagtatgt ag                                                          732

<210> SEQ ID NO 2
<211> LENGTH: 243
<212> TYPE: PRT
```

-continued

```
<213> ORGANISM: Streptococcus pneumoniae

<400> SEQUENCE: 2

Met Lys Leu Glu His Lys Asn Ile Phe Ile Thr Gly Ser Ser Arg Gly
 1               5                  10                  15

Ile Gly Leu Ala Ile Ala His Lys Phe Ala Gln Ala Gly Ala Asn Ile
            20                  25                  30

Val Leu Asn Ser Arg Gly Ala Ile Ser Glu Glu Leu Leu Ala Glu Phe
        35                  40                  45

Ser Asn Tyr Gly Ile Lys Val Val Pro Ile Ser Gly Asp Val Ser Asp
    50                  55                  60

Phe Ala Asp Ala Lys Arg Met Ile Asp Gln Ala Ile Ala Glu Leu Gly
65                  70                  75                  80

Ser Val Asp Val Leu Val Asn Asn Ala Gly Ile Thr Gln Asp Thr Leu
                85                  90                  95

Met Leu Lys Met Thr Glu Ala Asp Phe Glu Lys Val Leu Lys Val Asn
            100                 105                 110

Leu Thr Gly Ala Phe Asn Met Thr Gln Ser Val Leu Lys Pro Met Met
        115                 120                 125

Lys Ala Arg Glu Gly Ala Ile Ile Asn Met Ser Ser Val Val Gly Leu
    130                 135                 140

Met Gly Asn Ile Gly Gln Ala Asn Tyr Ala Ala Ser Lys Ala Gly Leu
145                 150                 155                 160

Ile Gly Phe Thr Lys Ser Val Ala Arg Glu Val Ala Ser Arg Asn Ile
                165                 170                 175

Arg Val Asn Val Ile Ala Pro Gly Met Ile Glu Ser Asp Met Thr Ala
            180                 185                 190

Ile Leu Ser Asp Lys Ile Lys Glu Ala Thr Leu Ala Gln Ile Pro Met
        195                 200                 205

Lys Glu Phe Gly Gln Ala Glu Gln Val Ala Asp Leu Thr Val Phe Leu
    210                 215                 220

Ala Gly Gln Asp Tyr Leu Thr Gly Gln Val Ile Ala Ile Asp Gly Gly
225                 230                 235                 240

Leu Ser Met
```